US008142474B2

(12) United States Patent
Hafner

(10) Patent No.: US 8,142,474 B2
(45) Date of Patent: Mar. 27, 2012

(54) TUBULAR SHAFT INSTRUMENT

(75) Inventor: Dieter Hafner, Tübingen (DE)

(73) Assignee: Erbe Elektromedizin GmbH, Tübingen (DE)

(*) Notice: Subject to any disclaimer, the term of this patent is extended or adjusted under 35 U.S.C. 154(b) by 372 days.

(21) Appl. No.: 12/444,356

(22) PCT Filed: Sep. 26, 2007

(86) PCT No.: PCT/EP2007/008386

§ 371 (c)(1), (2), (4) Date: Apr. 3, 2009

(87) PCT Pub. No.: WO2008/040483

PCT Pub. Date: Apr. 10, 2008

(65) Prior Publication Data

US 2010/0030213 A1 Feb. 4, 2010

(30) Foreign Application Priority Data

Oct. 5, 2006 (DE) ......................... 10 2006 046 919
Oct. 5, 2006 (DE) ......................... 10 2006 046 920
Oct. 5, 2006 (DE) ......................... 10 2006 047 204
Oct. 5, 2006 (DE) ......................... 10 2006 047 215
Nov. 29, 2006 (DE) ......................... 10 2006 056 405
Dec. 14, 2006 (DE) ......................... 10 2006 059 175

(51) Int. Cl.
*A61B 17/04* (2006.01)

(52) U.S. Cl. ........................... 606/207; 606/51; 606/174

(58) Field of Classification Search .............. 606/42–52, 606/170, 174, 205–209
See application file for complete search history.

(56) References Cited

U.S. PATENT DOCUMENTS 5,431,674 A * 7/1995 Basile et al. .................. 606/170
5,556,407 A * 9/1996 Wurster et al. ................ 606/174
6,905,497 B2 6/2005 Truckai et al.
2003/0114851 A1 6/2003 Truckai et al.

FOREIGN PATENT DOCUMENTS

| | | |
|---|---|---|
| DE | 42 04 051 | 8/1993 |
| DE | 44 44 166 | 6/1996 |
| DE | 10 2004 026 179 | 12/2005 |
| EP | 0 717 960 | 6/1996 |
| EP | 717960 A2 * | 6/1996 |
| EP | 1 211 995 | 6/2002 |
| EP | 1 557 132 | 7/2005 |
| WO | WO 98/26723 | 6/1998 |

OTHER PUBLICATIONS

English translation of the Written Opinion of the International Searching Authority issued on Apr. 28, 2009 in Intl. Appl. No. PCT/EP2007/008386 (filing date: Sep. 26, 2007).
International Search Report for PCT/EP2007/008386 dated Jan. 15, 2008.
Written Opinion for PCT/EP2007/008386, Jan. 15, 2008.
German Examination Report dated Dec. 14, 2006.

* cited by examiner

*Primary Examiner* — Laura Bouchelle
(74) *Attorney, Agent, or Firm* — Dickstein Shapiro LLP

(57) ABSTRACT

The invention relates to tubular shaft instruments, which are provided with a handle, a tubular shaft and a tool head. The tool head usually has two mouth parts, which can be displaced in relation to one another for gripping and fixing tissue. The invention discloses a slotted guide system for forming the articulation, said system having a virtual fulcrum outside the tubular shaft instrument.

26 Claims, 10 Drawing Sheets

Fig. 1
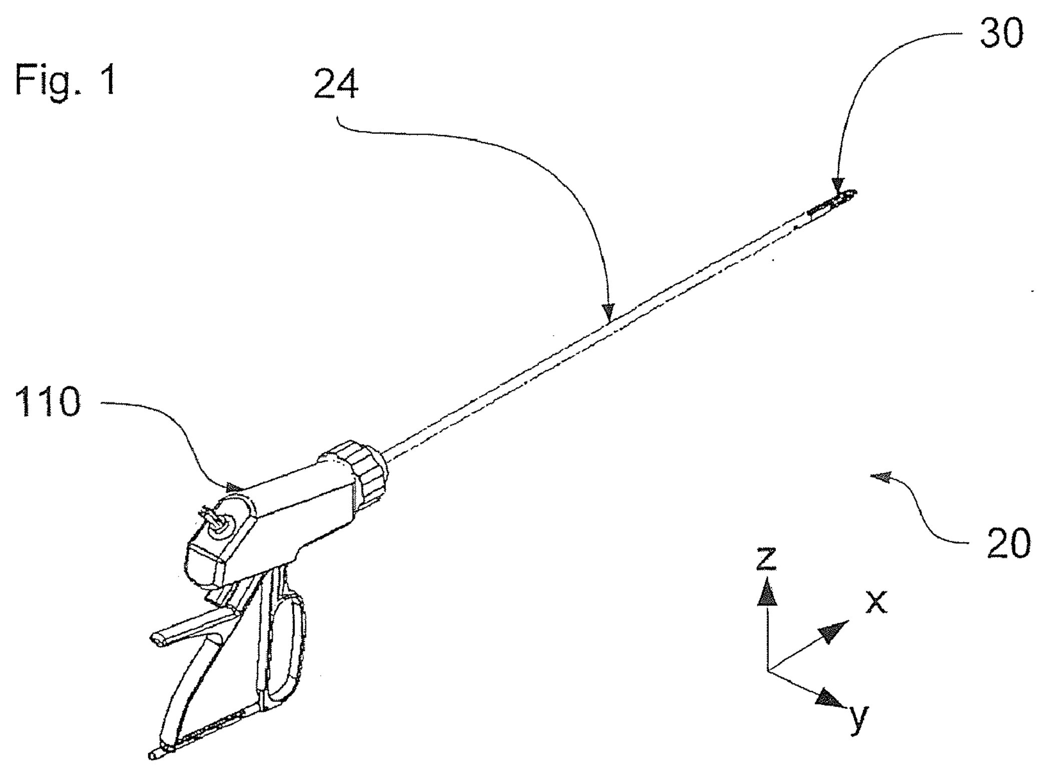
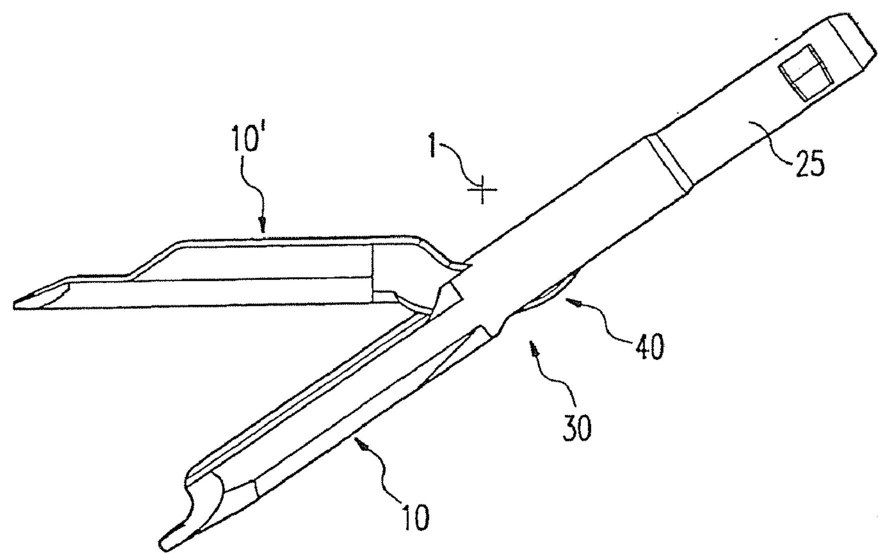
Fig. 2

50
51
56
52
24

103
102
100
101

50
52
54
51

50
52
54
51
54

50
52
54
51

TUBULAR SHAFT INSTRUMENT

BACKGROUND OF THE INVENTION

The invention relates to a tubular shaft instrument.

In modern medicine, attempts are generally made to keep the damage to intact tissue to a minimum. Thus, when circumstances permit, minimally invasive surgery is usually the preferred method used to perform an operative intervention. Small incisions and little trauma to the tissue lead to a lower sensation of pain after the operation and to rapid recovery and mobilisation of the patient. This also applies to laparoscopic surgery during which complex operations are performed in the abdominal cavity.

Operations of this type and the instruments required for them present a particular challenge to the manufacturers of medical instruments as the majority of the operative steps are performed in very restricted spaces and without direct visual contact. Thus the medical instruments used must not only be able to operate in the smallest spaces but must also function so reliably that visual monitoring is superfluous. The instruments are preferably constructed such that even without visual contact the operating surgeon always has feedback which enables him to draw conclusions about the progress of the operation.

Tubular shaft instruments are known which comprise a handle, a tubular shaft and at least two mouth parts. These tubular shaft instruments are suitable for gripping and fixing tissue. These tubular shaft instruments frequently have other functionalities. Thus, EP 1 211 995 B1, for example, discloses a tubular shaft instrument having corresponding mouth parts which applies high-frequency ("HF") current to the fixed tissue in order to coagulate it. It is also known to provide such tubular shaft instruments having a cutting device for separating the gripped tissue.

As tubular shaft instruments are used in very restricted regions of the body, they must be kept as small as possible. Nevertheless, as already observed, a reliable method of functioning and a high level of functionality must be guaranteed. Thus, amongst other things, it is problematic to ensure a sufficiently steady transmission of force for operating the mouth parts.

BRIEF DESCRIPTION OF THE DRAWINGS

The invention will be described in the following based on embodiments which will be explained in greater detail by means of drawings.

FIG. 1 illustrates a tubular shaft instrument for separating tissue according to a disclosed embodiment.

FIG. 2 illustrates the tool head of the tubular shaft instrument from FIG. 1, comprising a first and a second mouth part according to a disclosed embodiment.

The same reference numerals are used in the following description for identical parts and parts acting in an identical manner.

DETAILED DESCRIPTION OF THE INVENTION

Figure 3:
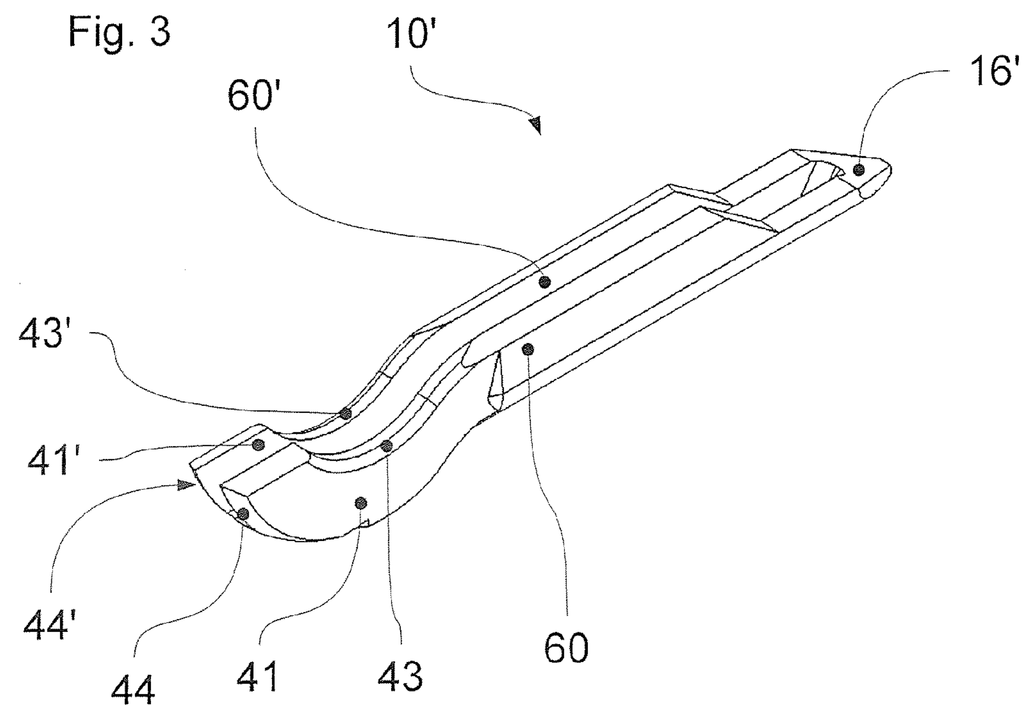
FIG. 3 illustrates the second mouth part in a perspective lateral view according to a disclosed embodiment.

An object of the present invention is to provide a tubular shaft instrument, which is easy to produce, has a long service life and has extremely functional characteristics.

This object is achieved by a tubular shaft instrument which comprises:

a tubular shaft, a first and a second mouth part on a distal end of the tubular shaft each having at least one clamping surface, and at least one articulation for rotatably supporting the mouth parts in such a manner that the mouth parts may be brought from an open position into a closed position in order to fix a tissue, whereby the articulation is designed in such a manner that a fulcrum of the articulation is located outside the mouth parts and the distal end of at least one mouth part is displaceable away from the distal end of the tubular shaft on opening of the mouth parts.

A substantial idea of the present invention is thus to provide an articulation by means of which the mouth parts are rotatably displaceable in relation to each other about a fulcrum. This fulcrum is ultimately virtual and is located outside, preferably above the oblong mouth parts. Due to this relocated virtual fulcrum, at least one of the two mouth parts experiences not only a rotary motion but also a translation motion.

The translatory movement is oriented such that on opening of the mouth parts, the distal tip of one of the mouth parts travels distally in relation to the tubular shaft instrument in sections at least. A movement in the opposite direction takes place on closing. Thus the moving mouth part feeds tissue, which is located between both mouth parts, towards the tubular shaft on closing. Thus a larger area of tissue may be gripped.

In addition, it is possible due to relocation of the fulcrum to ensure improved transmission of forces. Since the control cable used to operate the displaceable mouth part is usually attached directly to said mouth part, the further the attachment point is from the fulcrum, the greater the supporting lever effect for operating the mouth parts.

Preferably, the articulation includes a slotted guide system, i.e. at least one of the two mouth parts is guided by means of a permanently predefined structure. In this case the slotted guide system determines the displacement of the relevant mouth part. Limited by appropriate means, the mouth part glides along a profile which gives rise to the translatory and rotary motion.

Preferably, the articulation includes an articulation guide on one of the two mouth parts and at least one rail or groove on the other of the two mouth parts. In this case the rail or groove prescribes the displacement path of the relevant mouth part. The articulation guide engages in the rail or groove and guides the mouth part along the displacement path. Usually, such slotted guide systems have a broadly pronounced contact region by way of which the sections of the articulation, which are displaceable in relation to one another, engage with one another. Thus such articulations are significantly more stable and can absorb greater forces. As there is no transmission of force at a single point, these articulations usually have a longer service life.

In a preferred embodiment, the tubular shaft instrument comprises at least two partial articulations, which are spaced apart from one another to form a passage disposed preferably centrally between the articulations. A further advantage of the slotted guide system is that this may be disposed in a relatively space-saving manner. A particularly positive effect arises if at least two partial articulations are used in order to guide the mouth part. The twin design is not only particularly stable but it also enables the provision of passages through the actual centre of the articulation in which supply lines or additional instruments, such as a blade for separating tissue, may be guided.

Preferably, the tubular shaft instrument includes a blade for separating the fixed tissue. This blade may be guided by means of a suitable guide device through the tissue fixed by means of the mouth parts. The passages described make it possible to position the guide directly through the centre of the articulation.

Preferably, at least one mouth part comprises a blade guide for the blade. Thus the mouth part, for example, is designed in pairs in such a manner that said blade is guided centrally between the adjacent sections of the mouth part. This prevents torsion or tilting of the blade or cutter.

Preferably, one of the two mouth parts is rigidly connected to the tubular shaft. Although it is conceivable to attach both mouth parts rotatably to the tubular shaft and thus to ensure the opening and closing of both mouth parts, It is better, however, to join one of the two mouth parts directly to the tubular shaft so that this mouth part constitutes an extension of the tubular shaft. The second mouth part may then be attached by means of the articulation either to the tubular shaft, or to the other mouth part. Due to the rigid connection, the tubular shaft instrument can be more easily and securely operated.

Preferably, a substantially linearly displaceable strip or a force transmission device is provided for opening and closing of a mouth part to be displaced, said strip or device being attached by means of a resilient end section on the mouth part to be displaced. In a preferred embodiment, this is a tension strip, the end section of which is permanently connected to the mouth part. The strip that is bendable about the fulcrum winds itself around the mouth part on rotational movement of the mouth part about the virtual fulcrum. The push and pull movements, which are transmitted by the force transmission element to the mouth part to be displaced, thus always act tangentially to a circle about the fulcrum. With a convex design of the mouth part to be displaced, on the side on which the actuating element rests, there is a guarantee of a regular transmission of force regardless of the position of the mouth part to be displaced.

The strip is preferably made of spring steel.

Preferably, the strip is attached on the mouth part by means of welding, whereby the weld preferably runs out of square or curved in relation to a longitudinal axis of the strip, that is to say not at right angles thereto. The strip is thus disposed in such a manner on the mouth part to be displaced that the latter's longitudinal axis lies substantially perpendicular to the fulcrum. The weld runs along the fulcrum but describes a curve or angle such that the weld is formed to be as long as possible. Thus the effective force is distributed over as long a distance as possible. As a result of this, the device's durability may be increased significantly. Alternatively, the weld may have a corrugated shape.

In a further embodiment, a pin is inserted into a hole in the tension strip and additionally welded in place. The mouth part to be displaced thus includes a tension strip pin and the tension strip has a corresponding drilled hole.

Preferably, at least one of the clamping surfaces includes an electrode for coagulation of the fixed tissue. The tubular shaft instrument is thus a monopolar or bipolar terminal, by means of which the tissue fixed between the clamping surfaces is not only mechanically but also electrically cauterised.

Preferably, at least one of the mouth parts is made of electrically insulating material, in particular of ceramic material, in the region of the articulation at least. The mouth parts may thus be cast and subsequently sintered. Manufacture by the injection moulding method is conceivable. This type of production is to be preferred particularly when forming said rail or groove, that is to say the articulation. By forming the articulation at least in sections from an electrically insulating material, the clamping surfaces at least of the mouth parts are electrically insulated against each other and may be used without further measures as electrodes for coagulation.

FIG. 1 provides a rough overview of an embodiment of a tubular shaft instrument 20 according to the invention. It shows three functional components of the tubular shaft instrument 20, a handle 110, a longish tubular shaft 24 and a tool head 30 disposed on the distal end of tube shaft 24. Tool head 30 provides the tubular shaft instrument's actual functionality. It is used for cutting and/or coagulating tissue. Handle 110 controls the movement of tool head 30. In particular, mouth parts 10, 10' (cf. FIG. 2) may be closed as well as opened by means of handle 110 for fixing, coagulating and cutting tissue.

FIG. 2 shows an embodiment of a tool head 30 according to the invention, comprising a first mouth part 10 and a second mouth part 10'. First mouth part 10 is an oblong body having on its side facing tubular shaft 24 an adapter 25, which is rigidly joined to said tubular shaft 24. Second mouth part 10' is attached to first mouth part 10 by way of an articulation 40 and may be brought from an open position for seizing the tissue into a closed position for fixing the tissue. Articulation 40 is designed such that a virtual fulcrum 1 or pivot is located outside first and second mouth parts 10, 10'. Unlike conventional articulations 40 for such instruments, fulcrum 1 is not, therefore, located in the region where mouth parts 10, 10' engage or in tubular shaft 24 close to the longitudinal axis of tube shaft 24. The mechanism of articulation 40 illustrated acts such that a virtual fulcrum 1 is created above the side of the tubular shaft instrument which faces second mouth part 10'.

Figure 4:
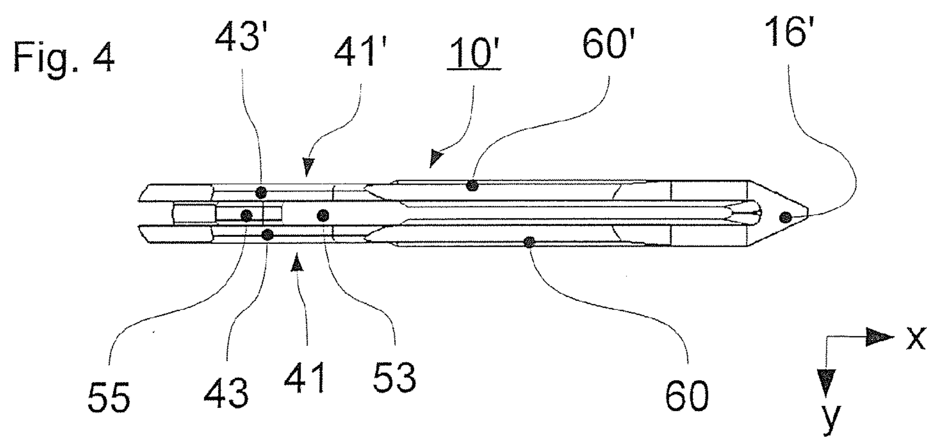
FIG. 4 illustrates the second mouth part in a view from above according to a disclosed embodiment.
Figure 9:
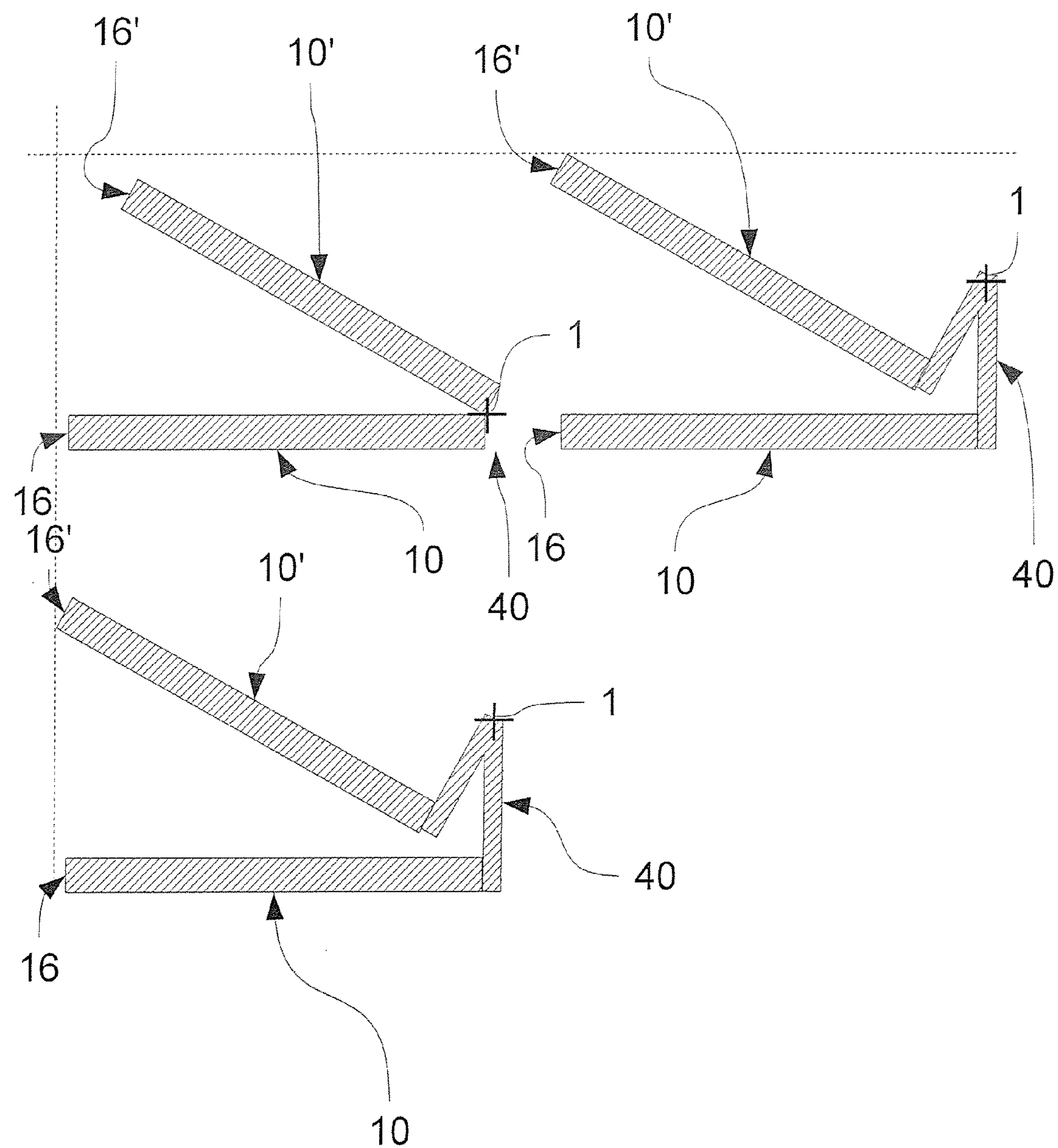
FIG. 9 illustrates a schematic diagram of two different articulations according to a disclosed embodiment.

The particular advantages of such a relocated fulcrum 1 are shown on the basis of the schematic diagrams of FIG. 9. Illustrated in the top left-hand corner is a conventional articulation, the fulcrum 1 of which is located substantially on the longitudinal axes of mouth parts 10 and 10'. In the open position, tip 16' of second mouth part 10' is offset backwards in relation to tip 16 of first mouth part 10. However, this is not the case with articulation 40 according to the invention, which is shown schematically in the other two diagrams of FIG. 9. Here fulcrum 1 is located noticeably above the longitudinal axes of both oblong mouth parts 10, 10'. With the same opening in respect of the angle formed by first mouth part 10 in relation to second mouth part 10', tip 16' of second mouth part 10' is located substantially on or in front of a perpendicular straight line through tip 16 of first mouth part 10 even in the open state. If second mouth part 10' is opened in relation to first mouth part 10, there is thus not only a rotary displacement during which the relative alignment of second mouth part 10' changes in relation to first mouth part 10 but there is also a longitudinal displacement of second mouth part 10' which is oriented distally, that is to say parallel to the longitudinal axis of first mouth part 10 in the direction of its tip 16. Conversely, during a closing movement of mouth parts 10, 10', there is a longitudinal displacement of second mouth part 10' in the proximal direction. As a result of this, tissue which is located between both mouth parts 10, 10', is ultimately drawn into tool head 30 (see FIG. 2). Furthermore, according to the invention, the lift of second tip 16, that is to say the distance between first and second tip 16, 16', is considerably greater with the same opening angle (cf. FIG. 9, right-hand side). In one embodiment, the length of mouth parts 10, 10' in relation to the distance of the longitudinal axis of first mouth part 10 to the fulcrum is in the ratio of approx. 10:1. Whilst in FIG. 9 relocated fulcrum 1 is achieved, for the sake of clarification, by way of extensions attached vertically on the proximal ends of mouth parts 10, 10', in a preferred embodiment the formation of fulcrum 1 is purely virtual. This virtual design is achieved by a slotted guide system as is explained below on the basis of FIGS. 3-8. Thus, as shown in FIG. 3, second mouth part 10' has two curved articulation guide rails 41, 41' on its proximal end opposing tip 16". Seen from above (c. FIG. 4), these articulation guide rails 41, 41' run substantially parallel along the longitudinal axis of second mouth part 10' and are spaced apart to form a channel.

Seen from the side (cf. FIG. 5), second mouth part 10' has a spoon-shaped profile. The proximal end of second mouth part 10', in particular articulation guide rails 41, 41', thus each have on their upper side a concave section 43, 43', which engages with first mouth part 10. As can be seen from FIG. 6, to achieve this mouth part 10 has two articulation guide pins 42, 42', each of which has a convex structural section. During the opening and closing movement of mouth parts 10, 10', concave section 43 of first articulation guide rail 41 slides over the adjacent, convex section of first articulation guide pin 42 and concave section 43' of second articulation guide rail 41* slides over the adjacent, convex section of second articulation guide pin 42'. The curvature of concave sections 43, 43' of both articulation guide rails 41, 41' and the corresponding sections of articulation guide pins 42, 42' are determining for the position of virtual fulcrum 1. With a more pronounced curvature, fulcrum 1 lies closer to tool head 30 than with a less pronounced curvature. The effects described in respect of FIG. 9 occur correspondingly more or less pronounced.

Compared to articulations that only have a single-point connection, the guide mechanisms or articulation 40 additionally have the advantage of high stability. Due to the convex and concave sections which engage with each other, a large-area contact region is formed and articulation 40 can absorb significantly more force than an articulation with a single-point connection. To further stabilise articulation 40, first mouth part 10 (see FIGS. 6-8) comprises a first articulation guide bearing 46 and a second articulation guide bearing 46'. Like articulation guide pins 42, 42', articulation bearings 46, 46' are attached alternately on the inside of the sidewalls of first mouth part 10.

First articulation guide bearing 46 and first guide pin 42 are spaced apart such that they accommodate first articulation guide rail 41 in the space between them. First articulation guide bearing 46 has a concave cross-section, which engages with convex section 44 of first articulation guide rail 41. On opening and closing tool head 30, first articulation guide rail 41, guided by first guide pin 42 and first articulation guide bearing 46, rotates about fulcrum 1 (see FIG. 5).

Figure 5:
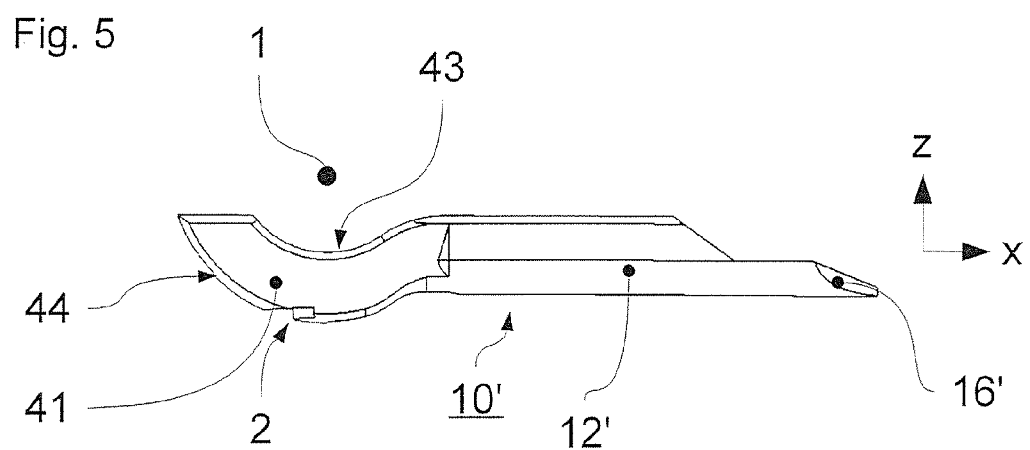
FIG. 5 illustrates the second mouth part in a lateral view according to a disclosed embodiment.
Figure 6:
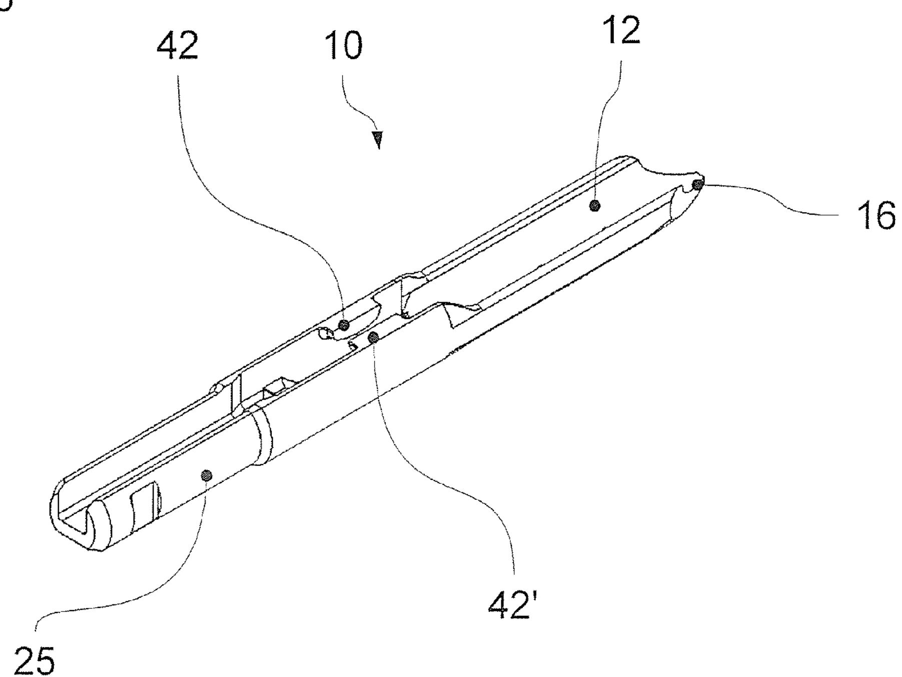
FIG. 6 illustrates the first mouth part in a perspective lateral view according to a disclosed embodiment.
Figure 7:
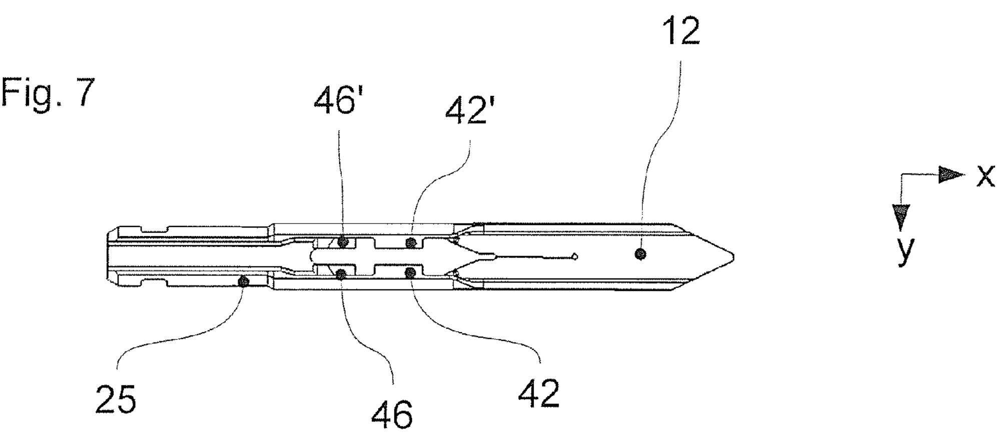
FIG. 7 illustrates the first mouth part in a view from above according to a disclosed embodiment.
Figure 8:
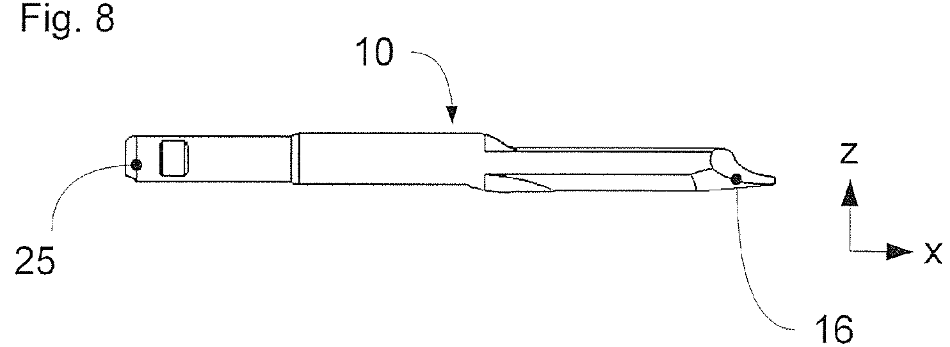
FIG. 8 illustrates the first mouth part in a lateral view according to a disclosed embodiment.

Likewise, second articulation guide rail 41', guided by second guide pin 42' and articulation guide bearing 46', rotates about fulcrum 1 (see FIG. 5). For this, second articulation guide rail 41', second articulation guide pin 42', a convex section 44' of second articulation guide rail 41' and second articulation guide bearing 46' are designed and disposed symmetrically to first articulation guide rail 41, first articulation guide pin 42, convex section 44 of first articulation guide rail 41 and first articulation guide bearing 46.

Figure 10:
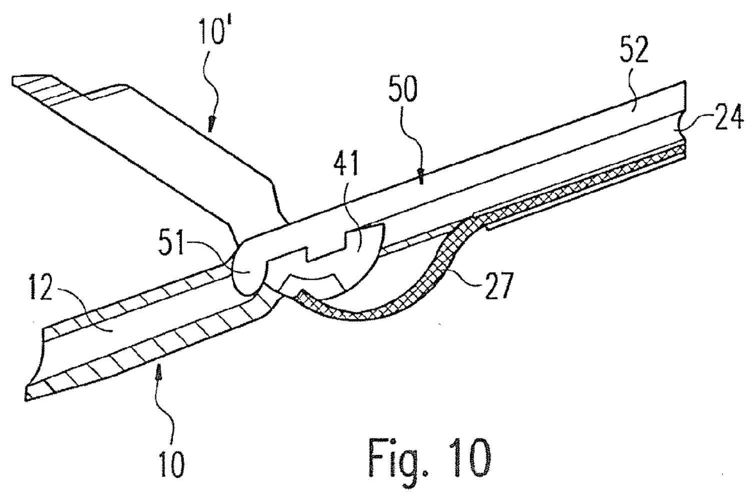
FIG. 10 illustrates a cross-section through the tool head from FIG. 2 with a cutting device according to a disclosed embodiment.
Figure 19:
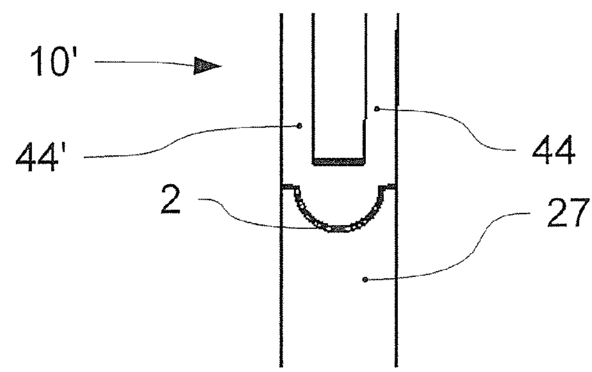
FIG. 19 illustrates the second mouth part with tension strip according to a disclosed embodiment.

As shown in FIG. 10, a tension strip 27 is attached on the proximal end of second mouth part 10'. More precisely, it is attached approximately centrally on convex sections 44, 44' of articulation guide rails 41, 41'. To achieve this, articulation guide rails 41, 41' have a profile for forming an abutting edge 2 (FIG. 5). Preferably, this abutting edge 2 does not run in a straight line parallel to fulcrum 1 but is designed in a semicircular shape (cf. FIG. 19). Due to this elongated abutting edge 2, along which second mouth part 10' and tension strip 27 are welded, the transmission of force into tension strip 27 is homogenised and the tensile and flexural loading capacity of the weld is significantly increased. In alternative embodiments, acute-angled welds or welds with multiple serrations, which provide a comparable result, are conceivable. Tension strip 27 is substantially wider than it is thick parallel to fulcrum 1. This ensures resilience and bendability of tension strip 27 on rotation of second mouth part 10'. In the longitudinal direction of the tubular shaft instrument, however, tension strip 27 is relatively stiff such that shear forces may also be generated.

Figure 20:
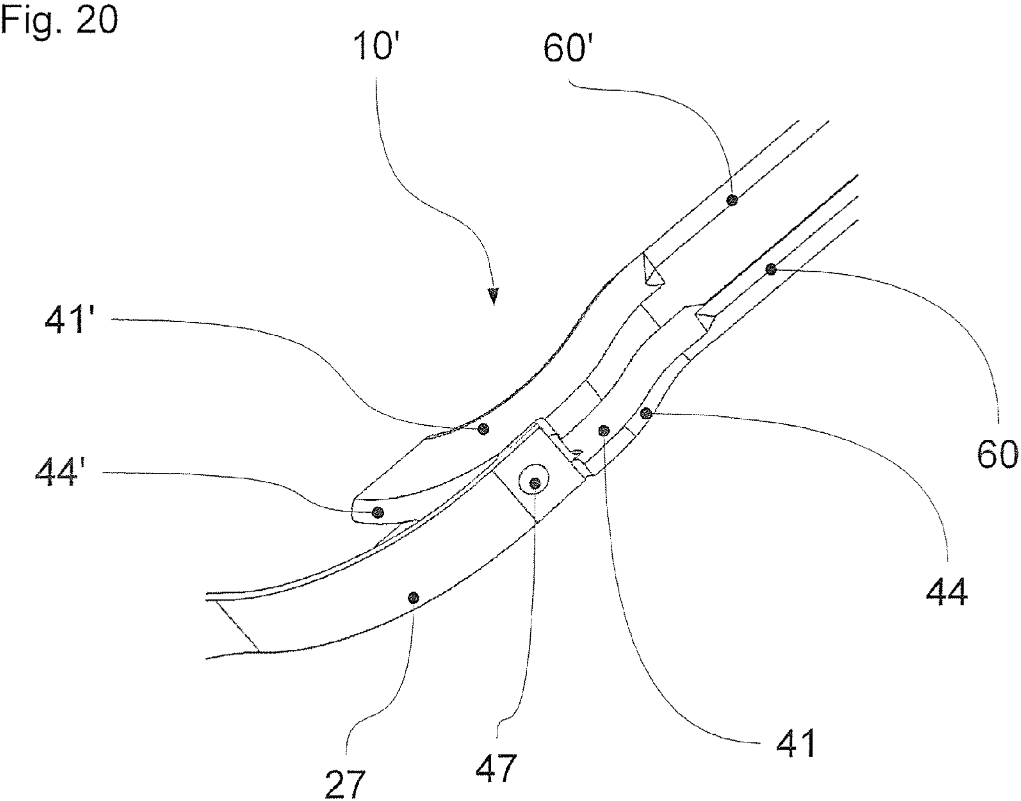
FIG. 20 illustrates the second mouth part (further embodiment) in a perspective lateral view according to a disclosed embodiment.
Figure 21:
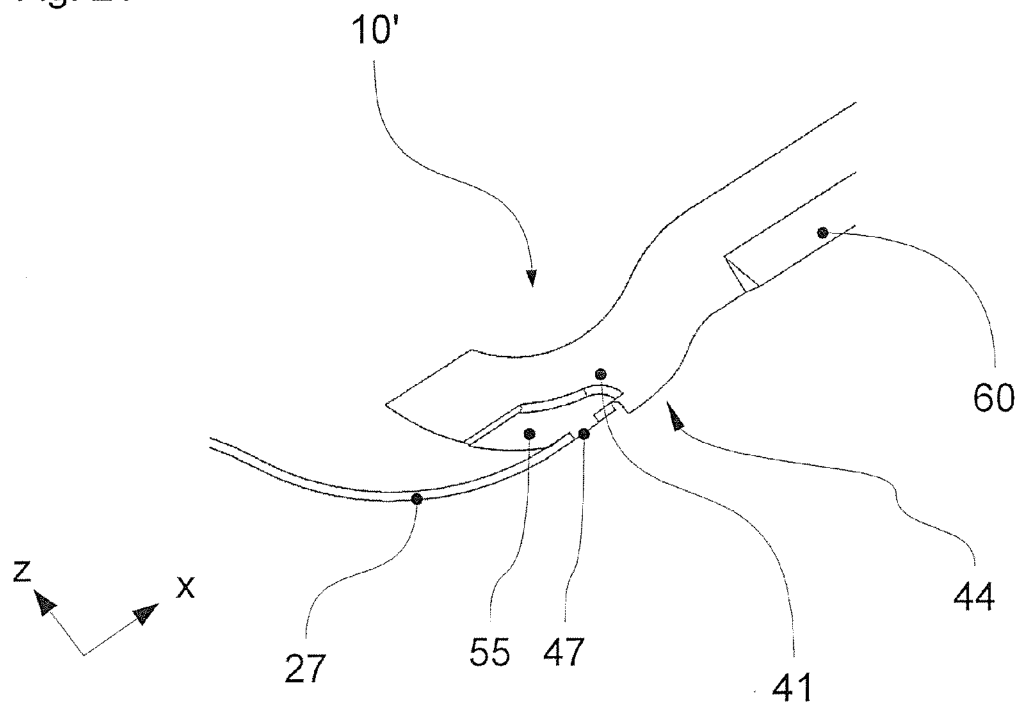
FIG. 21 illustrates section through the second mouth part from FIG. 20 according to a disclosed embodiment.

Alternatively, second mouth part 10', as shown in FIGS. 20 and 21, has a tension band pin 47, which runs substantially radially to fulcrum 1. This tension strip pin 47 is disposed centrally between convex sections 44, 44' of articulation guide rails 41, 41' and is accommodated in a hole of tension strip 27. Thus a permanent connection is created between mouth part 10' and tension strip 27. Additional welding increases the stability of the joint.

By attaching a first end of tension strip 27 to convex sections 44, 44' of articulation guide rails 41, 41', it is ensured that the tensile force exerted by means of tension strip 27 always acts substantially tangentially to the circular motion of curved articulation guide rails 41, 41' about fulcrum 1. Thus a uniform transmission of force independent of the opening angle is assured. A second end of tension strip 27 is operatively connected to handle 110 and may be displaced by means of a control device provided thereon. Due to virtual fulcrum 1, which, as already explained, is located outside and above mouth parts 10, 10', the distance between fulcrum 1 and the first end of tension strip 27 is significantly greater than the distance achieved with normal articulations. Thus the embodiment of the tubular shaft instrument described has a significantly higher leverage by means of which second mouth part 10' may be moved over tension strip 27.

Both mouth parts 10, 10' each have a clamping surface 12, 12' for fixing the tissue. First mouth part 10 thus has, on a distal section, a first clamping surface 12 which faces upwards. First clamping surface 12 is formed substantially concave transverse to the longitudinal axis of first mouth part 10. In the closed state of tool head 30, convex second clamping surface 12' of second mouth part 10' lies substantially parallel to this first clamping surface 12.

In the embodiment described, these clamping surfaces 12, 12' are not only suitable for securely fixing the tissue to be cut later, they also form the electrodes for a coagulation process. To achieve this, sections of clamping surfaces 12, 12' are electrically conductive and connected via printed conductors to a high-frequency current source, which is also controllable byway of handle 110. Thus the tissue gripped may be cauterised to such an extent prior to the cutting procedure that separation is possible without bleeding. Preferably, sections at least of mouth parts 10, 10' are manufactured from ceramic material by the injection moulding method. Thus the guide elements, in particular articulation guide rails 41, 41' and articulation guide pins 42, 42' of articulation 40, are easy to form. Articulation 40 of ceramic material forms an electrical insulation between mouth parts 10, 10', in particular between their electrodes for coagulation.

Figure 11:
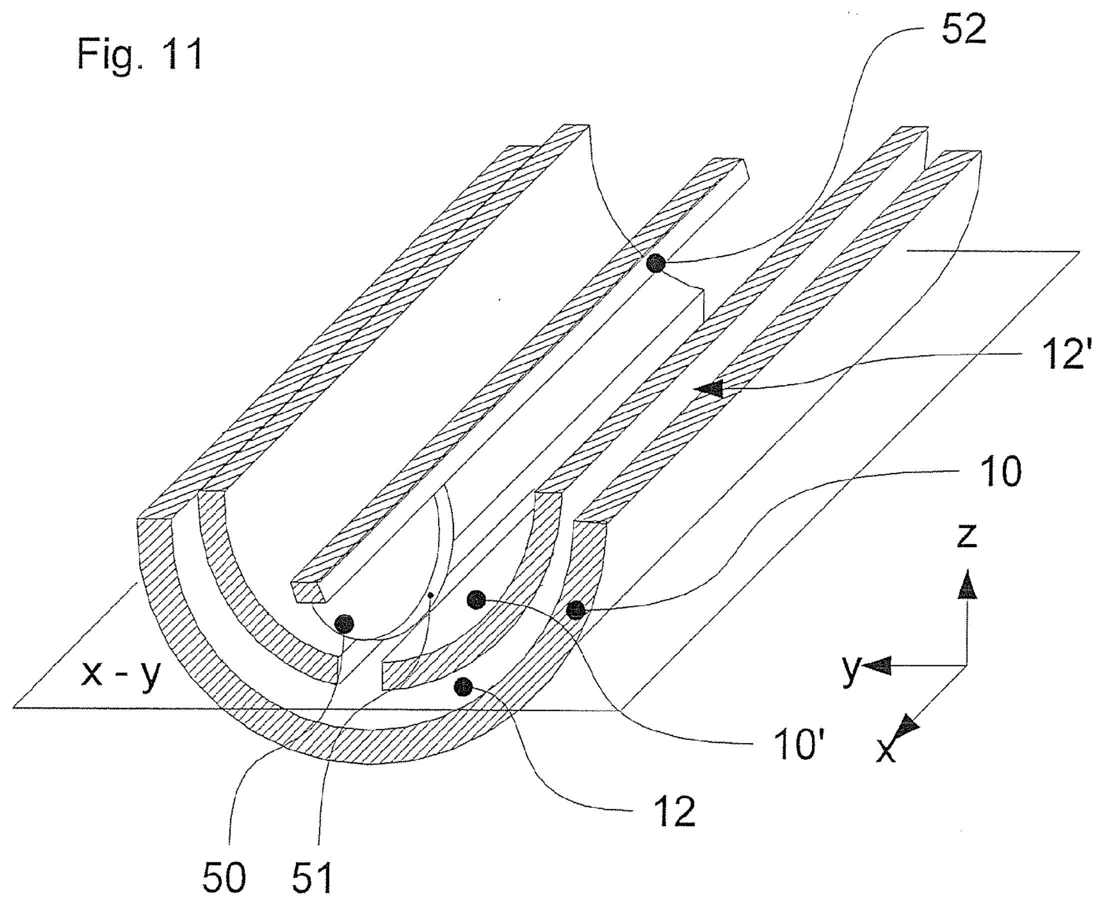
FIG. 11 illustrates a schematic diagram of the cutting device according to a disclosed embodiment.

In the present embodiment, the actual mechanical cutting process takes place after coagulation. To achieve this, a cutting device 50 is moved parallel to a fixing plane x-y (cf. FIG. 11), which is defined by clamping surfaces 12, 12'. This cutting device 50 comprises a blade 51 for separating the tissue in addition to a guide wire 52 by means of which a displacement of blade 51 in the longitudinal direction of the tubular shaft instrument (x-axis) is possible.

Prior to the cutting process, blade 51 is drawn back so far towards tubular shaft 24 that premature injury of the tissue is not possible. Preferably, the blade in first mouth part 10 is at the level of articulation guide pins 42, 42'. From this starting position, blade 51 is brought onto fixing plane x-y by way of a ramp 55 integrated in second mouth part 10' (cf. FIG. 4 for this). This ramp 55 is located between the two articulation guide rails 41, 41'. Second mouth part 10' provides a blade guide 53 for the displacement of blade 51 or the cutter. This blade guide 53 is an oblong opening extending along the longitudinal axis of second mouth part 10'. In order to hold blade 51 perpendicular to fixing plane x-y, second mouth part 10' has in its central region side parts 60, 60', which are disposed parallel to each other in such a way that they form a channel extending lengthways. Blade 51 or the cutter is guided in this channel.

Figure 12:
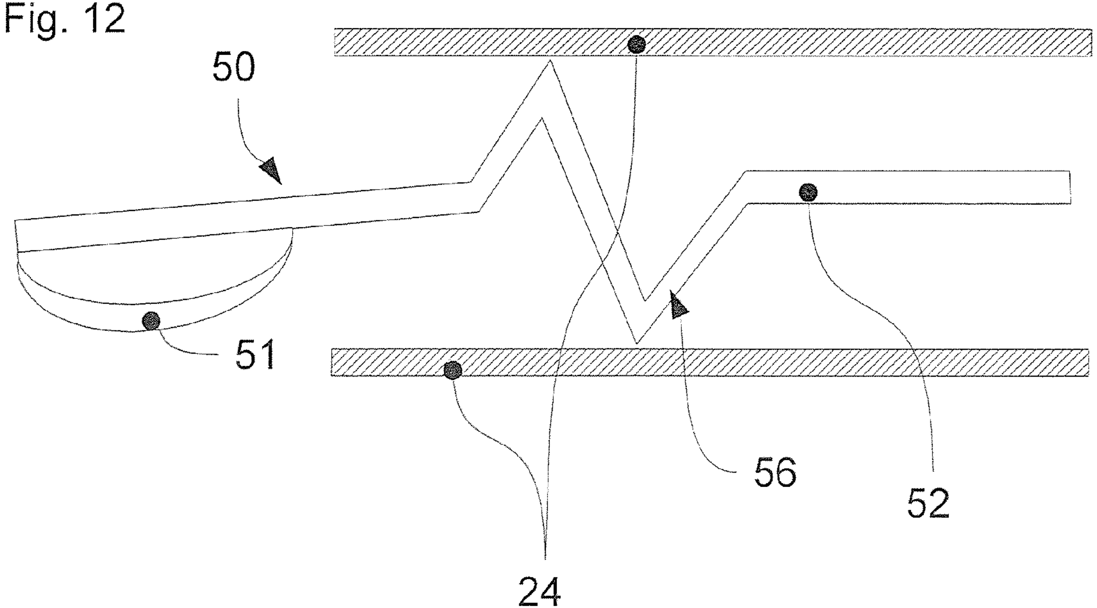
FIG. 12 illustrates a schematic view of the cutting device in a tubular shaft of a tubular shaft instrument according to a disclosed embodiment.

After closing mouth parts 10, 10', blade 51 thus glides out of its starting position over ramp 55 into said channel and may there be pulled or pushed distally and proximally over the tissue. Blade 51 is preloaded in relation to fixing plane x-y in order to ensure that this displacement separates the tissue step by step. A preloading device exerts a force perpendicular to fixing plane x-y, which presses blade 51 against the plane. This force is built up via the resilience of guide wire 52 and its curvature. As can be seen from FIG. 12, guide wire 52 is curved perpendicular to fixing plane x-y in the plane preloaded by blade 51. A crimp 56 is located in a front section of guide wire 52. Crimp 56 is integrated in guide wire 52 in such a manner that in the fully extended state of cutting device 50, that is to say when blade 51 is at the distal end of mouth parts 10, 10', the crimp in tubular shaft 24 is likewise at the distal end of said shaft. Crimp 56 is used to transfer at least part of the force exerted by the curvature of guide wire 52 perpendicular to fixing plane x-y to tubular shaft 24 and has corresponding contact points. The curvature of guide wire 52 is provided such that if the proximal end of the guide wire runs parallel to tubular shaft 24, the distal end of unattached guide wire 52 is curved downwards and blade 51 lies at least partially below fixing level x-y. Guide wire 52 is operatively connected to handle 110 in such a manner that blade 51 can be moved back and forth in tool handle 30 by means thereof.

The most varied embodiments are conceivable in respect of the design of blade 51. These will be described in the following on the basis of FIGS. 13, 14 and 15. One idea of the invention is that blade 52 has at least one section which runs substantially parallel to fixing plane x-y and thus parallel to the fixed tissue. Consequently, during the cutting procedure blade 51 glides over the tissue until it is completely separated. Unlike in conventional cutting procedures, it can thus be ensured that even when blade 51 is blunt the tissue will be separated and will not be crushed due to the mechanical pressure. The section of the cutting blade formed parallel to fixing plane x-y likewise has the advantage that blade 51 rests on the tissue not only at a point but usually over a longer region. Therefore wearing of blade 51 at certain points is prevented.

Figure 13:
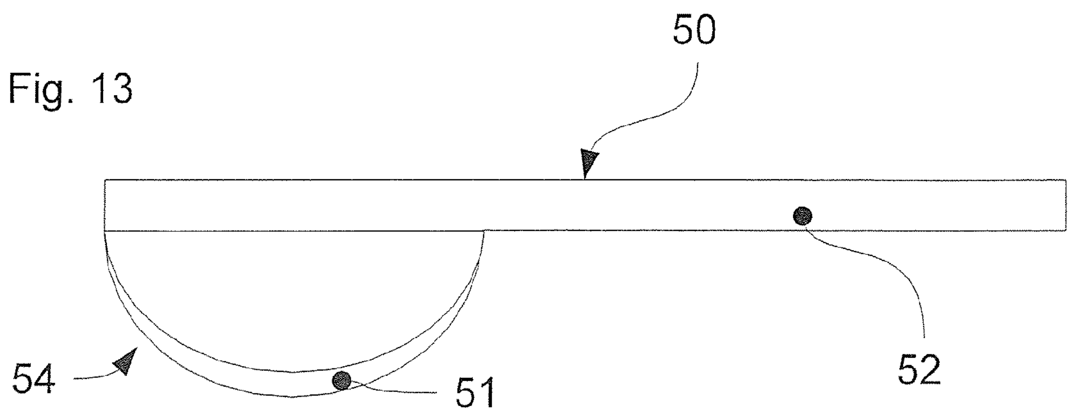
FIG. 13-15 illustrate three embodiments of a cutting blade according to a disclosed embodiment.

FIG. 13 shows a semicircular blade 51, having a convex curvature. Blade 51 is disposed on the underside of guide wire 52. It has a blade curvature 54 distal and proximal to the tubular shaft instrument.

Figure 14:
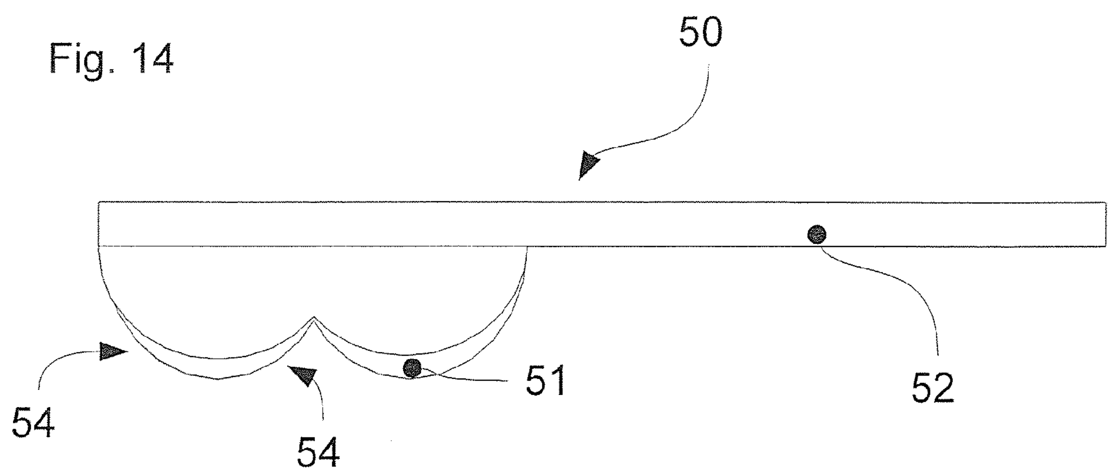

FIG. 14 shows a blade 51, comprising two semicircles each disposed one behind the other.

Figure 15:
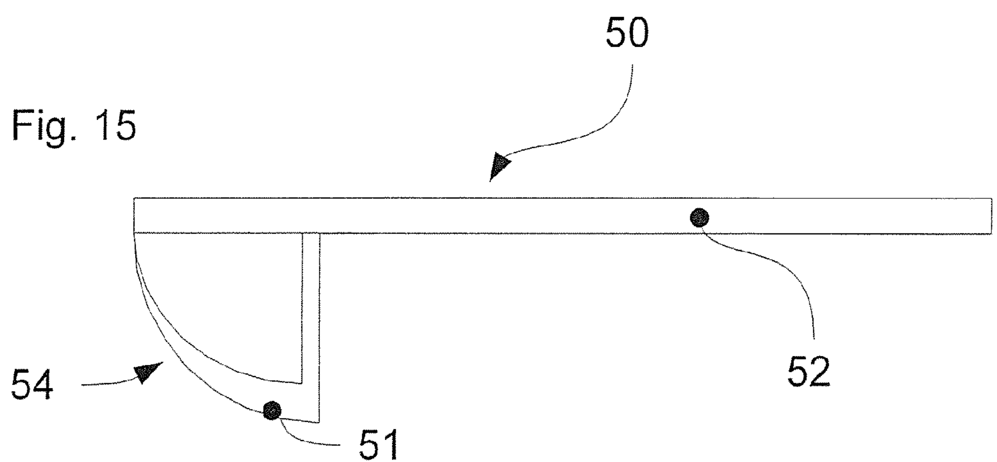

FIG. 15 shows a blade 51, having a blade curvature 54 distally, and a section perpendicular to guide wire 52 proximally.

Preferably, blade 51 is microtoothed overall.

In an alternative embodiment (cf. FIG. 10 for example), guide wire 52 is a rail. The rail may be designed in such a manner that it has the same functionality as guide wire 52. Preloading in relation to fixing plane x-y may be achieved by means of the rails intrinsic resilience or by means of a separate device (e.g. a spring).

The advantageous cutting device 50 of the invention has been described so far in conjunction with the advantageous articulation shape. Both inventions, however, may also be executed separately from one another.

Figure 17:
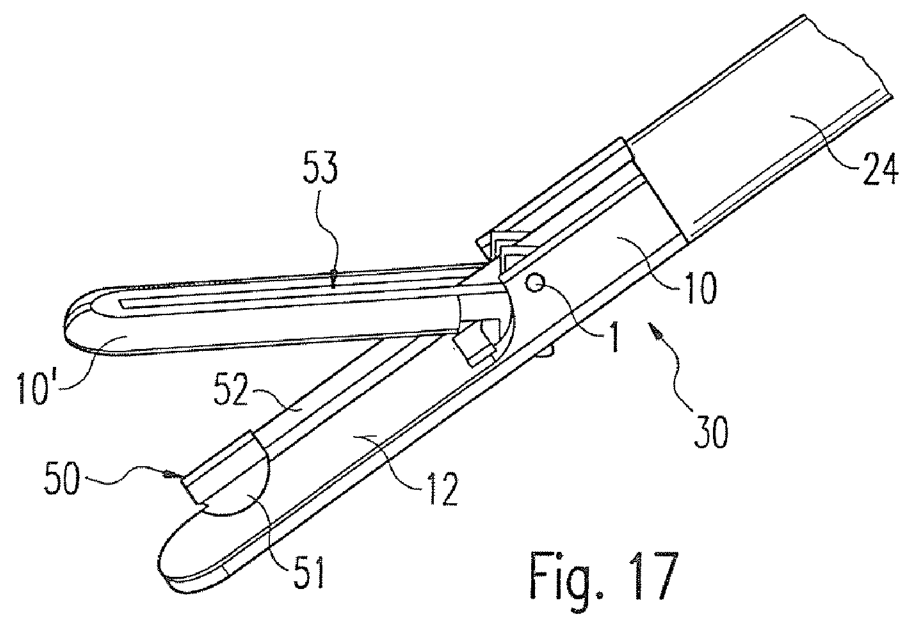
FIG. 17 illustrates a perspective view of a tool head in an open position according to a disclosed embodiment.
Figure 18:
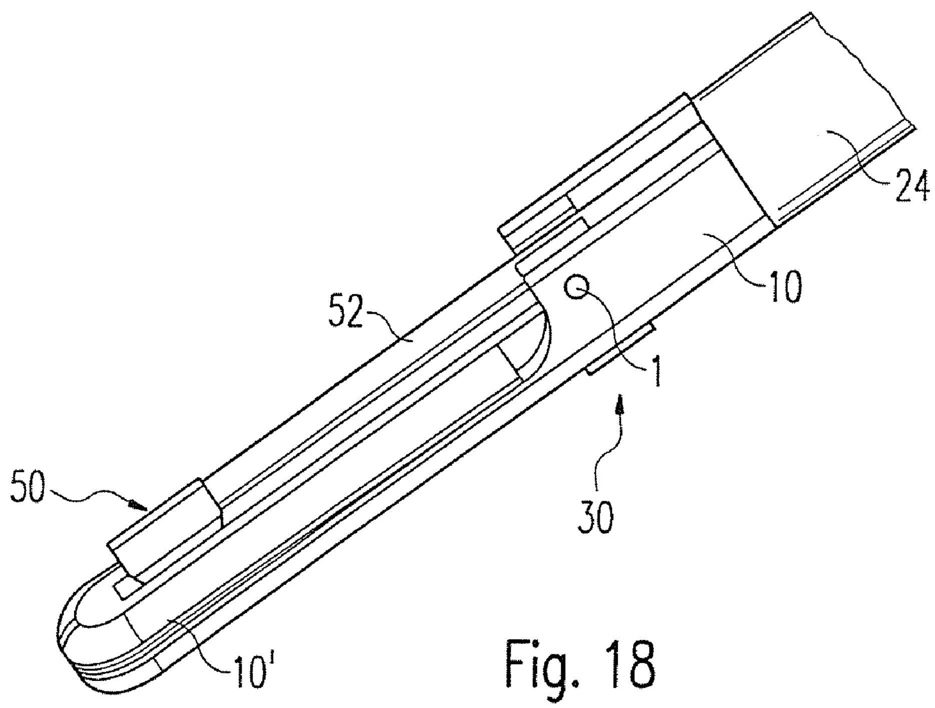
FIG. 18 illustrates the tool head from FIG. 17 in a closed position according to a disclosed embodiment.

Thus, FIGS. 17 and 18, for example, show cutting device 50 in a tool head 30, whereby second mouth part 10' is not in operative connection with first mouth part 10 by way of a slotted guide system. Here fulcrum 1 lies substantially on the longitudinal axis of mouth parts 10, 10'.

Figure 16:
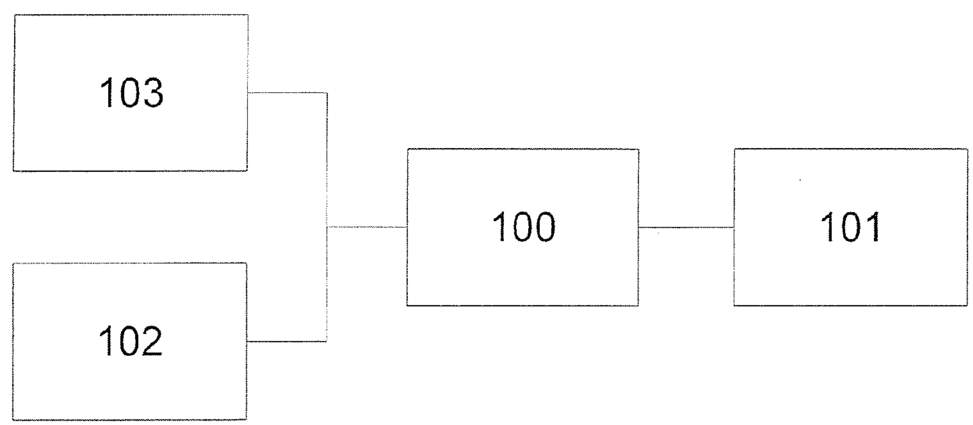
FIG. 16 illustrates a block diagram of an incision monitoring device according to a disclosed embodiment.

In one embodiment according to the invention, the tubular shaft instrument further comprises a cut monitoring device. This determines when the tissue between the two clamping surfaces 12, 12' is completely separated. In the embodiment, blade 51 rests on first clamping surface 12 when the tissue is completely separated. As clamping surface 12 comprises an electrode for coagulation, it is electrically conductive in parts at least. According to the invention, at least one section of blade 51, which mechanically contacts separating surface 12 when the tissue is separated, is likewise formed of electrically conductive material. The electrical contact between blade 51 and clamping surface 12 is determined by means of a cut monitoring device. The gripped tissue is deemed to be completely separated when a continuous electrical contact exists between blade 51 and clamping surface 12 during a complete cutting movement by tip 16' of second mouth part 10' up to ramp 55. As can be seen from FIG. 16, the cut monitoring device comprises a processing unit 100, a display device 101, a switch 103 and a travel sensor 102 for determining and displaying the progress of the cutting procedure. Travel sensor 102 determines the position or displacement of blade 51 and consequently helps to define an observation period that preferably covers a complete blade movement. Switch 103 is formed in the simplest case by means of electrically conductive blade 51 and first clamping surface 12. As the tissue to be cut has a certain electrical conductivity, electric switch 103 is only deemed to be closed when a low-ohm connection exists between clamping surface 12 and blade 51. A corresponding device is connected upstream of processing unit 100. If processing unit 100 ascertains that there is a continuous low-ohm contact between blade 51 and clamping surface 12 during a complete observation period, it indicates to the user by means of display device 101 that the gripped tissue has been separated completely. Therefore cutting device 50 is treated with care since the displacement of blade 51 over clamping surface 12 without tissue sandwiched between damages the device.

Alternatively, it may also be constantly indicated to the user whether there is a direct mechanical contact between blade 51 and clamping surface 12. As the user performs the movement of blade 51 manually, he can draw conclusions independently as to whether the tissue is adequately separated.

In a further embodiment, travel sensor 102 comprises two electrical contact regions on the distal and proximal end of blade guide 53, which are designed in such a manner that it is possible to determine contacting between blade 51 and the distal contact region as well as between blade 51 and the proximal contact region. Processing unit 100 can thus determine the start and end of the observation interval.

Figure 22:
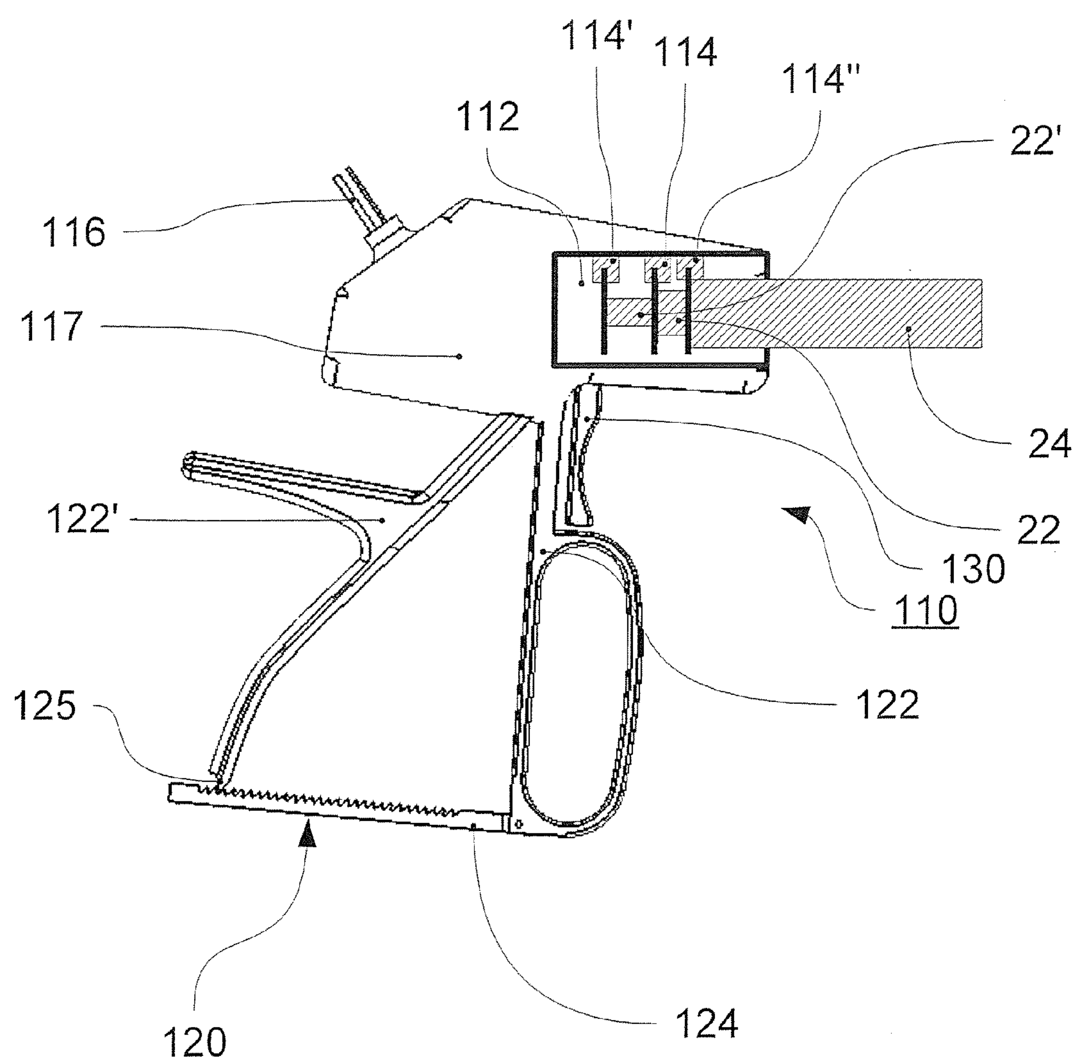
FIG. 22 illustrates a schematic lateral view of the tubular shaft instrument according to a disclosed embodiment.

FIG. 22 shows a schematic detail view of handle 110 from FIG. 1. Handle 110 comprises a handle body 117 on the underside of which a first handle lever 122 is integrally formed. This handle lever 122 has an opening for receiving a plurality of fingers, preferably the middle, ring and little finger. A second handle lever 122' is rotatably joined to handle body 117 close to first handle lever 122. Mouth parts 10, 10' of tool head 30 may be opened and closed by means of a displacement of second handle lever 122' relative to first handle lever 122 proximally and distally. Handle levers 122, 122' form a hand trigger 120 and can thus be grasped in the user's hand such that the entire tubular shaft instrument can be guided with one hand. To achieve this, the hand encloses sections of handle lever 122, 122'. Located on the end of second handle lever 122' facing away from handle body 117 is an extension which engages in a toothed rack 124. This toothed rack 124 is attached at a right angle to the longitudinal axis of first handle lever 122 on its end facing away from handle body 117. The toothing of toothed rack 124 is designed in such a manner that second handle lever 122' can be moved step by step towards handle lever 122 and the position correspondingly set remains without the continued exertion of a force. In order to release this fastening of handle levers 122, 122' to each other, toothed rack 124 is pressed away from extension 125 in such a manner that they are no longer engaged.

Moreover, handle 110 has a finger trigger 130, which is likewise rotatably attached to handle body 117. Cutting device 50, in particular blade 51, may be displaced distally by operating finger trigger 130. A spring element (not illustrated) inside handle body 117 returns finger trigger 130 to its starting position after operation, as a result of which cutting device 50 is displaced proximally. Finger trigger 130 is disposed distally in front of first handle lever 122 in such a manner that finger trigger 130 can be operated with the first finger on grasping handle levers 122, 122'.

Handle 110 has a momentary contact switch 116 on the proximal side of handle body 117, which controls the coagulation current. In an alternative embodiment, it is possible in place of momentary contact switch 116 to provide a control device having a plurality of actuating elements by means of which a plurality of coagulation modes may be selected and performed. It is likewise conceivable to provide display device 101 on handle body 117.

In one embodiment according to the invention, tubular shaft 24 and handle 110 are designed in such a manner that tubular shaft 24 may be detachably inserted into handle 110. To achieve this, a receiving opening 112, which can be closed by means of a cover, is located on the side of handle 110.

Thus, prior to the operation, a sterile disposable tubular shaft 24 having appropriate tool head 30 and cutting device 50 is inserted into reusable handle 110 and locked therein. Reuse of tubular shaft 24 and the associated devices is not envisaged. Handle body 117 has a first coupling element 114 or a coupling element, a second coupling element 114' or a coupling element and a third coupling element 114" or a coupling element for mechanical connection of tool head 30, cutting device 51 and tubular shaft 24. A ring provided on the proximal end of tubular shaft 24 engages with third coupling element 114" in such a manner that the tubular shaft is rigidly connected to handle body 117. A first inner tube adapter 22 engages, by means of a ring likewise disposed on the proximal end, with first coupling element 114, which is in operative connection with second handle lever 122'. The displacement of second handle lever 122' is transferred to first coupling element 114 by means of a mechanism disposed inside handle body 117 and transfers this displacement in turn to first inner tube adapter 22. This is directly or indirectly joined mechanically to second mouth part 10' by way of tension strip 27. A longitudinal displacement of first inner tube adapter 22 in relation to tubular shaft 24 thus brings about opening and closing of mouth parts 10, 10'.

A second inner tube adapter 22' is disposed movably in relation to first inner tube adapter 22 inside said first inner tube. This inner tube adapter 22' is operatively connected to guide wire 52 and displaces blade 51. Inserting tubular shaft 24 into handle body 117 engages a proximal ring on the end of second inner tube adapter 22' with second coupling element 114' and transfers the displacement or the force exerted by means of finger trigger 130 to cutting device 50.

In order to make it easier to insert disposable tubular shaft 24, a removable fastening is provided thereon, which holds inner tube adapter 22, 22' in a predetermined position relative to tubular shaft 24, which is designed in such a manner that the rings are easily insertable into coupling elements 114, 114', 114".

Coupling elements 114, 114', 114" are designed in such a manner that tubular shaft 24 may be rotated in relation to handle 110. Thus the alignment of tool head 30 can be adjusted freely in relation to handle 110. During rotation, the rings of inner tube adapters 22, 22' and of tubular shaft 24 rotate in coupling elements 114, 114', 114" and thus form an articulation.

LIST OF REFERENCE NUMBERS

1 Fulcrum
2 Abutting edge
10, 10' Mouth part
12, 12° Clamping surface
16, 16' Tip
20 Tubular shaft instrument
22, 22' Inner tube adapter 24 Tubular shaft
25 Adapter
27 Tension strip
30 Tool head
40 Articulation
41, 41' Articulation guide rail
42, 42' Articulation guide pin
43, 43' Concave section of the articulation guide rail
44, 44' Convex section of the articulation guide rail
46, 46' Articulation guide bearing
47 Tension strip pin
50 Cutting device
51 Blade
52 Guide wire
53 Blade guide
54 Blade curvature
55 Ramp
56 Crimp
60, 60'. Side part
100 Processing unit
101 Display device
102 Travel sensor
103 Switch
110 Handle
112 Receiving opening
114, Coupling element
116 Momentary contact switch
117 Handle body
120 Hand trigger
122, Handle lever
124 Toothed rack
125 Extension
130 Finger trigger
x x-axis
y y-axis
z z-axis

The invention claimed is:

1. A tubular shaft instrument for gripping and/or coagulating and/or separating tissue, comprising:
- a tubular shaft;
- a first and a second mouth part on a distal end of the tubular shaft each having at least one clamping surface;
- at least one articulation for rotatably supporting the mouth parts in such a manner that the mouth parts may be brought from an open position into a closed position in order to fix the tissue using the clamping surfaces; and
- a strip that can be displaced substantially linearly for opening and closing of the first mouth part, the strip being attached by means of a resilient end section to the first mouth part,
- wherein the articulation includes a slotted guide system,
- wherein the slotted guide system is configured so that a virtual fulcrum of the articulation is located at a distance from the longitudinal axis of the tubular shaft and the distal end of the first mouth part is displaceable away from the distal end of the tubular shaft on opening the mouth parts, and
- wherein the first mouth part rotates around the virtual fulcrum on opening of the first mouth part.

2. The tubular shaft instrument according to claim 1, wherein the articulation includes an articulation guide on one of the two mouth parts and at least one rail or groove on the other of the two mouth parts.

3. The tubular shaft instrument according to claim 1, wherein the at least one articulation comprises at least two partial articulations which are spaced apart from one another to form a passage disposed centrally between said partial articulations.

4. The tubular shaft instrument according to claim 1, further comprising a blade for separating the fixed tissue.

5. The tubular shaft instrument according to claim 4, wherein at least one mouth part includes a blade guide.

6. The tubular shaft instrument according to claim 1, wherein one of the two mouth parts is rigidly connected to the tubular shaft.

7. The tubular shaft instrument according to claim 1, wherein the strip is designed as a tension strip, the end section of which is permanently attached to the mouth part.

8. The tubular shaft instrument according to claim 7, wherein the strip is comprised of spring steel.

9. The tubular shaft instrument according to claim 1, wherein at least one of the clamping surfaces includes an electrode for coagulation of the fixed tissue.

10. The tubular shaft instrument according to claim 1, wherein at least one of the mouth parts comprises, at least in the region of the articulation, an electrically insulating material.

11. The tubular shaft instrument according to claim 10, wherein the electrically insulating material is a ceramic material.

12. The tubular shaft instrument according to claim 1, wherein one of the two mouth parts comprises a blade guide extending along the cutting direction.

13. The tubular shaft instrument according to claim 12, wherein the blade guide is a ramp-shaped blade guide which is disposed such that, by moving in the direction of cutting, the blade guide brings a blade out of a starting position at a distance from a fixing plane onto the fixing plane.

14. The tubular shaft instrument according to claim 12, wherein the blade guide is configured such that a blade may be brought into a starting position close to the fulcrum of the mouth parts.

15. The tubular shaft instrument according to claim 1, wherein the tissue is fixed by means of the clamping surface in a fixing plane, whereby a cutting device having a blade for cutting tissue is disposed opposite one of the mouth parts and is displaceable over a predeterminable cutting path substantially parallel to the fixing plane.

16. The tubular shaft instrument according to claim 15, further comprising a first electrode and a second electrode disposed in such a manner on the cutting device and/or the clamping surface that a mechanical contact between blade and clamping surface is ascertainable by means of a processing unit connected to the electrodes.

17. The tubular shaft instrument according to claim 1, wherein the tubular shaft instrument is an electrosurgical tubular shaft instrument.

18. A tubular shaft instrument for gripping and/or coagulating and/or separating tissue, comprising:
- a tubular shaft;
- a first and a second mouth part on a distal end of the tubular shaft each having at least one clamping surface;
- at least one articulation for rotatably supporting the mouth parts in such a manner that the mouth parts may be brought from an open position into a closed position in order to fix the tissue using the clamping surfaces; and
- a strip that can he displaced substantially linearly for opening and closing of a mouth part to be displaced, said strip being attached by means of a resilient end section on the mouth part to be displaced,
- wherein the articulation is configured so that a fulcrum of the articulation is located outside the mouth parts and the distal end of at least one mouth part is displaceable away from the distal end of the tubular shaft on opening of the mouth parts, and wherein the strip is attached to the mouth part by means of welding.

19. The tubular shaft instrument according to claim 18, wherein the strip is attached to the mouth part via a welding joint that is square in relation to a longitudinal axis of the strip.

20. The tubular shaft instrument according to claim 18, wherein the strip is attached to the mouth part via a welding joint that is curved in relation to a longitudinal axis of the strip.

21. A tubular shaft instrument for gripping and/or coagulating and/or separating tissue, comprising:

a tubular shaft;

a first and a second mouth part on a distal end of the tubular shaft each having at least one clamping surface; and at least one articulation for rotatably supporting the mouth parts in such a manner that the mouth arts may be brought from an open position into a closed position in order to fix the tissue using the clamping surfaces, wherein the articulation is configured so that a fulcrum of the articulation is located outside the mouth parts and the distal end of at least one mouth part is displaceable away from the distal end of the tubular shaft on opening of the mouth parts, wherein the mouth parts are configured to fix a tissue in a fixing plane, the tubular shaft instrument further comprising:

a cutting device having a blade for cutting the fixed tissue, the cutting device being displaceable in a cutting direction by means of an actuating device, the blade configured to be displaceably guided substantially parallel to the fixing plane and preloaded against the fixing plane during cutting by means of a preloading device, and wherein the preloading device comprises a resilient guide wire having a curvature, whereby the guide wire is substantially rigidly joined to the blade and is guided in the tubular shaft in such a manner that the blade is preloaded in relation to the tubular shaft in the direction of the fixing plane.

22. The tubular shaft instrument according to claim 21, wherein the preloading device includes a crimp which is disposed in the guide wire such that the crimp is close to the distal end of the tubular shaft when the blade is pushed forward.

23. A tubular shaft instrument for gripping and/or coagulating and/or separating tissue, comprising:

a tubular shaft;

a first and a second mouth part on a distal end of the tubular shaft each having at least one clamping surface; and at least one articulation for rotatably supporting the mouth parts in such a manner that the mouth parts may be brought from an open position into a closed position in order to fix the tissue using the clamping surfaces, wherein the articulation is configured so that a fulcrum of the articulation is located outside the mouth parts and the distal end of at least one mouth part is displaceable away from the distal end of the tubular shaft on opening of the mouth parts, wherein the mouth parts are configured to fix a tissue in a fixing plane, the tubular shaft instrument further comprising:

a cutting device having a blade for cutting the fixed tissue, the cutting device being displaceable in a cutting direction by means of an actuating device, the blade configured to be displaceably guided substantially parallel to the fixing plane and preloaded against the fixing plane during cutting by means of a preloading device, and wherein the preloading device includes a crimp which is disposed in the guide wire such that the crimp is close to the distal end of the tubular shaft when the blade is pushed forward.

24. A medical instrument, comprising:

a tubular shaft;

a first and a second mouth part on a distal end of the tubular shaft, each having at least one clamping surface;

at least one articulation for rotatably supporting the mouth parts in such a manner that the mouth parts may be brought from an open position into a closed position in order to fix a tissue in a fixing plane using the clamping surfaces;

a strip that can be displaced substantially linearly for opening and closing of the first mouth part, the strip being attached by means of a resilient end section to the first mouth part;

a cutting device having a blade for cutting tissue and is disposed opposite one of the mouth parts and is displaceable over a predeterminable cutting path substantially parallel to the fixing plane; and a first electrode and a second electrode disposed in such a manner on the cutting device and/or the clamping surface that a mechanical contact between blade and clamping surface is ascertainable by means of a processing unit connected to the electrodes, wherein the articulation includes a slotted guide system, wherein the slotted guide system is configured so that a virtual fulcrum of the articulation is located at a distance from the longitudinal axis of the tubular shaft and the distal end of the first mouth part is displaceable away from the distal end of the tubular shaft on opening the mouth parts, wherein the first mouth part rotates around the virtual fulcrum on opening of the first mouth part, and wherein the blade comprises the first electrode, the clamping surface comprises the second electrode and the processing unit comprises a device for determining an electrical resistance between the electrodes.

25. The medical instrument according to claim 24, wherein the processing unit is configured so that a curve of the resistance is ascertainable during the cutting path.

26. The medical instrument according to claim 24, wherein the processing unit comprises a travel sensor and/or an electric switch for detecting the displacement of the blade parallel to the clamping surface.

* * * * *